US012201484B2

(12) United States Patent
Itkowitz et al.

(10) Patent No.: US 12,201,484 B2
(45) Date of Patent: Jan. 21, 2025

(54) SYSTEMS AND METHODS FOR PRESENTING AUGMENTED REALITY IN A DISPLAY OF A TELEOPERATIONAL SYSTEM

(71) Applicant: INTUITIVE SURGICAL OPERATIONS, INC., Sunnyvale, CA (US)

(72) Inventors: Brandon D. Itkowitz, San Jose, CA (US); Simon P. DiMaio, San Carlos, CA (US); Paul W. Mohr, Mountain View, CA (US); Theodore W. Rogers, Alameda, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/449,586

(22) Filed: Aug. 14, 2023

(65) Prior Publication Data
US 2023/0380926 A1 Nov. 30, 2023

Related U.S. Application Data

(63) Continuation of application No. 17/731,903, filed on Apr. 28, 2022, now Pat. No. 11,766,308, which is a (Continued)

(51) Int. Cl.
*A61B 90/00* (2016.01)
*A61B 34/00* (2016.01)
(Continued)

(52) U.S. Cl.
CPC ............ *A61B 90/36* (2016.02); *A61B 34/25* (2016.02); *A61B 34/35* (2016.02); *G06F 3/017* (2013.01);
(Continued)

(58) Field of Classification Search
None
See application file for complete search history.

(56) References Cited

U.S. PATENT DOCUMENTS 6,377,011 B1 * 4/2002 Ben-Ur ................... G06F 3/016
345/184
8,398,541 B2 3/2013 Dimaio et al.
(Continued)

FOREIGN PATENT DOCUMENTS

| CN | 102947774 A | 2/2013 |
| CN | 104349739 A | 2/2015 |

(Continued)

OTHER PUBLICATIONS

Extended European Search Report for Application No. 18871136.0, mailed on Oct. 18, 2021, 13 pages.
(Continued)

*Primary Examiner* — Martin Mushambo
(74) *Attorney, Agent, or Firm* — Haynes & Boone, LLP.

(57) ABSTRACT

A system comprises a processor and a memory having computer readable instructions stored thereon, which, when executed by the processor, cause the system to display an image of a surgical environment. The image includes an information icon corresponding to an instrument in the surgical environment. The instructions further cause the system to display an image of a body part of a user. The image of the body part is used to interact with the information icon. The instructions further cause the system to receive a gesture of the body part, via a gesture-based input device registering movement of the body part, to cause the image of the body part to interact with the information icon. The instructions further cause the system to display an (Continued)

information menu in the image of the surgical environment based on the interaction between the image of the body part and the information icon.

20 Claims, 12 Drawing Sheets

Related U.S. Application Data continuation of application No. 16/757,746, filed as application No. PCT/US2018/056422 on Oct. 18, 2018, now Pat. No. 11,351,005.

(60) Provisional application No. 62/575,759, filed on Oct. 23, 2017.

(51) Int. Cl.
    *A61B 34/35*     (2016.01)
    *G06F 3/01*     (2006.01)
    *G06T 19/00*     (2011.01)
    *A61B 1/00*     (2006.01)
    *A61B 17/00*     (2006.01)
    *A61B 17/02*     (2006.01)
    *A61B 34/10*     (2016.01)
    *A61B 90/50*     (2016.01)

(52) U.S. Cl.
    CPC ........ *G06T 19/006* (2013.01); *A61B 1/00045* (2013.01); *A61B 2017/00207* (2013.01); *A61B 2017/00973* (2013.01); *A61B 17/02* (2013.01); *A61B 2034/105* (2016.02); *A61B 2034/107* (2016.02); *A61B 34/74* (2016.02); *A61B 90/361* (2016.02); *A61B 2090/365* (2016.02); *A61B 2090/3762* (2016.02); *A61B 2090/502* (2016.02); *G06T 2210/41* (2013.01)

(56) References Cited

U.S. PATENT DOCUMENTS

| | | | |
|---|---|---|---|
| 8,520,027 B2 | 8/2013 | Itkowitz et al. | |
| 9,788,909 B2 | 10/2017 | Larkin et al. | |
| 9,833,254 B1* | 12/2017 | Barral | A61B 17/320068 |
| 9,858,475 B2 | 1/2018 | Itkowitz et al. | |
| 10,499,997 B2* | 12/2019 | Weinstein | A61B 34/20 |
| 10,650,594 B2* | 5/2020 | Jones | G06F 3/0346 |
| 11,351,005 B2 | 6/2022 | Itkowitz et al. | |
| 2004/0111183 A1* | 6/2004 | Sutherland | A61B 34/76 700/245 |
| 2009/0177452 A1* | 7/2009 | Ullrich | G06F 3/014 703/11 |
| 2011/0118753 A1 | 5/2011 | Itkowitz et al. | |
| 2011/0218774 A1* | 9/2011 | Ikits | G06F 3/016 703/1 |
| 2011/0264107 A1* | 10/2011 | Nikou | A61B 17/1633 700/258 |
| 2011/0282141 A1* | 11/2011 | Itkowitz | G06T 15/503 382/128 |
| 2012/0280988 A1* | 11/2012 | Lampotang | G09B 23/285 434/262 |
| 2013/0072787 A1 | 3/2013 | Wallace et al. | |
| 2013/0245375 A1 | 9/2013 | DiMaio et al. | |
| 2015/0032414 A1* | 1/2015 | Rozsa | G06F 3/011 702/167 |
| 2016/0324580 A1* | 11/2016 | Esterberg | A61B 34/10 |
| 2016/0331584 A1* | 11/2016 | Ren | A61B 3/13 |
| 2016/0349845 A1* | 12/2016 | Poupyrev | G06F 3/04845 |
| 2017/0108930 A1* | 4/2017 | Banerjee | A61B 34/72 |
| 2017/0154158 A1* | 6/2017 | Marka | G05B 19/048 |
| 2017/0186157 A1* | 6/2017 | Boettger | A61B 5/0013 |
| 2017/0203438 A1* | 7/2017 | Guerin | B25J 9/1605 |
| 2017/0273549 A1* | 9/2017 | Nazareth | A61B 1/06 |
| 2017/0287214 A1 | 10/2017 | Anderson et al. | |
| 2017/0348061 A1 | 12/2017 | Joshi et al. | |
| 2017/0367771 A1* | 12/2017 | Tako | G16H 20/40 |
| 2018/0078034 A1* | 3/2018 | Savall | A47B 21/03 |
| 2018/0092706 A1* | 4/2018 | Anderson | G06T 19/006 |
| 2018/0095542 A1* | 4/2018 | Mallinson | G06T 19/006 |
| 2019/0206134 A1* | 7/2019 | Devam | G06F 3/011 |
| 2019/0355278 A1* | 11/2019 | Sainsbury | A61B 34/30 |
| 2020/0138518 A1* | 5/2020 | Lang | A61B 90/37 |
| 2022/0249193 A1 | 8/2022 | Itkowitz et al. | |

FOREIGN PATENT DOCUMENTS

| | | |
|---|---|---|
| CN | 106293082 A | 1/2017 |
| KR | 20120098342 A | 9/2012 |
| WO | WO-2014176403 A1 | 10/2014 |
| WO | WO-2015095715 A1 | 6/2015 |
| WO | WO-2016133644 A1 | 8/2016 |
| WO | WO-2017031132 A1 | 2/2017 |
| WO | WO-2017114834 A1 | 7/2017 |

OTHER PUBLICATIONS

International Preliminary Report on Patentability for Application No. PCT/US2018/056422, mailed on May 7, 2020, 10 pages.
International Search Report and Written Opinion for Application No. PCT/US2018/056422, mailed on Feb. 1, 2019, 14 pages.
Partial Supplementary European Search Report for Application No. 18871136.0, mailed on Jul. 15, 2021, 14 pages.
Vertut. J., and Coiffet, P., "Robot Technology: Teleoperation and Robotics Evolution and Development." English translation, Prentice-Hall, Inc., Inglewood Cliffs, NJ, USA 1986, vol. 3A, 332 pages.

* cited by examiner

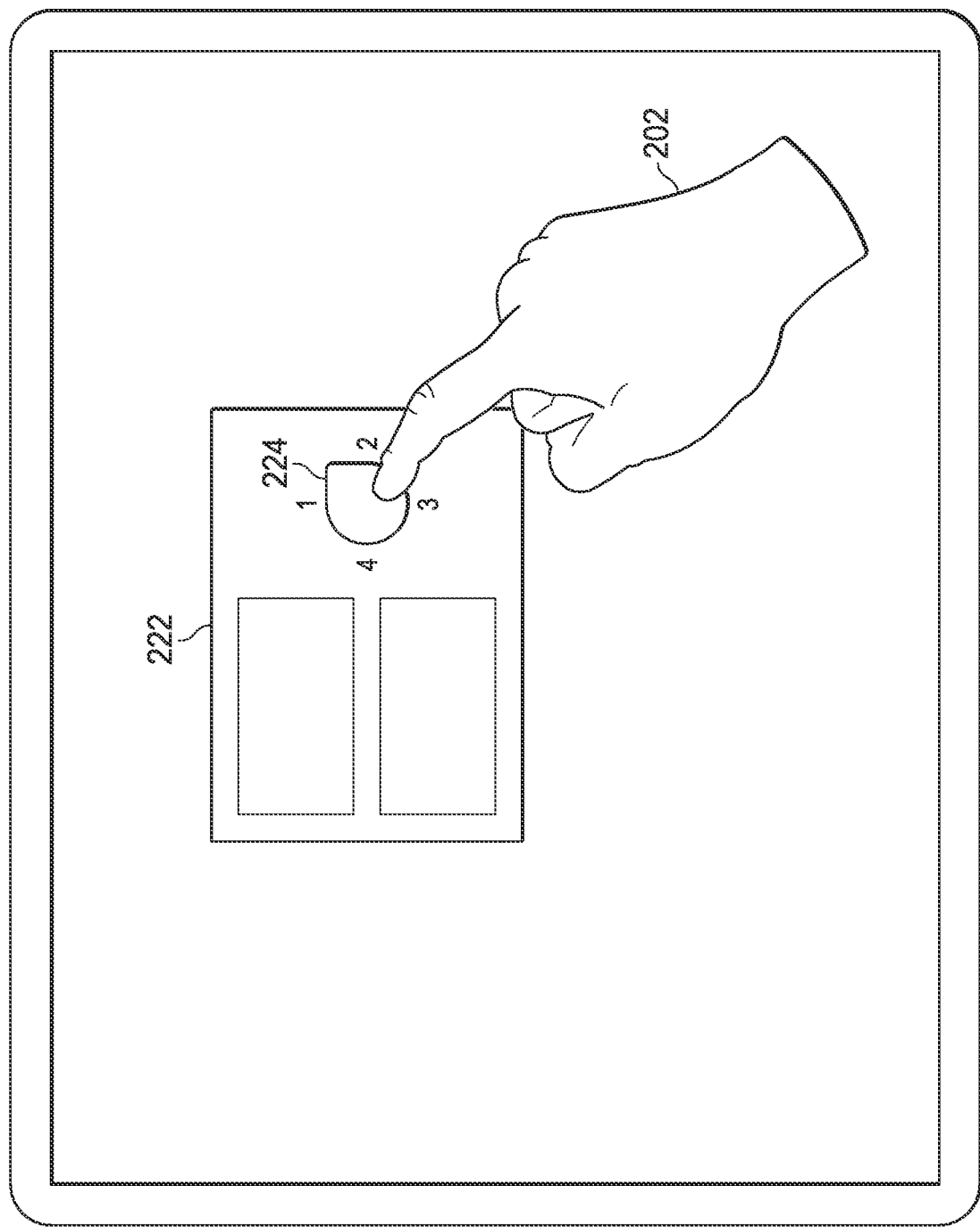

SYSTEMS AND METHODS FOR PRESENTING AUGMENTED REALITY IN A DISPLAY OF A TELEOPERATIONAL SYSTEM

CROSS-REFERENCE TO RELATED APPLICATIONS

This application is a continuation of U.S. patent application Ser. No. 17/731,903, filed Apr. 28, 2022, which is a continuation of U.S. patent application Ser. No. 16/757,746, filed Apr. 20, 2020, now U.S. Pat. No. 11,351,005, which is the U.S. National Phase of International Patent Application No. PCT/US2018/056422, filed Oct. 18, 2018, which designated the U.S. and claims priority to and the benefit of U.S. Provisional Application No. 62/575,759, filed Oct. 23, 2017, all of which are incorporated by reference herein in their entirety.

FIELD

The present disclosure is directed to systems and methods for performing a teleoperational medical procedure and more particularly to systems and methods for presenting augmented reality in a display of a teleoperational system.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. In existing teleoperational medical systems, the surgeon's view of his or her own extremities may be blocked by a display at a surgical control console, limiting the surgeon's awareness of body position relative to control input devices. Systems and methods are needed to augment the images on the display to create better body position awareness.

SUMMARY

The embodiments of the invention are summarized by the claims that follow below.

In one embodiment, a method comprises displaying a surgical environment image. The surgical environment image includes a virtual control element for controlling a component of a surgical system. The method also includes displaying an image of a body part of a user used to interact with the virtual control element. The method also comprises receiving a user input from the user with a gesture based input device while the body part interacts with the virtual control element. The method also comprises adjusting a setting of the component of the surgical system based on the received user input.

In another embodiment, a method comprises displaying a surgical environment image including a virtual marking element. The method also includes displaying a body part of a user used to interact with the virtual marking element. The method also includes receiving a user input from the user with a gesture based input device while the body part interacts with the virtual marking element and generating a patient anatomy mark on a patient anatomy based on the received user input.

In another embodiment, a method comprises displaying an image of an internal patient anatomy on a display while a patient is located in a surgical environment. The image of the internal patient anatomy is received from a first imaging device. The method also includes displaying an image of the surgical environment external of the patient anatomy on the display while the patient is located in the surgical environment. The image of the surgical environment external of the patient anatomy is received from a second imaging device. The displayed image of the internal patient anatomy is at least partially surrounded by the displayed image of the external patient anatomy.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4B illustrates a cursor image of a user's extremity interacting with an image of a component in the surgical environment.

DETAILED DESCRIPTION

Figure 1A:
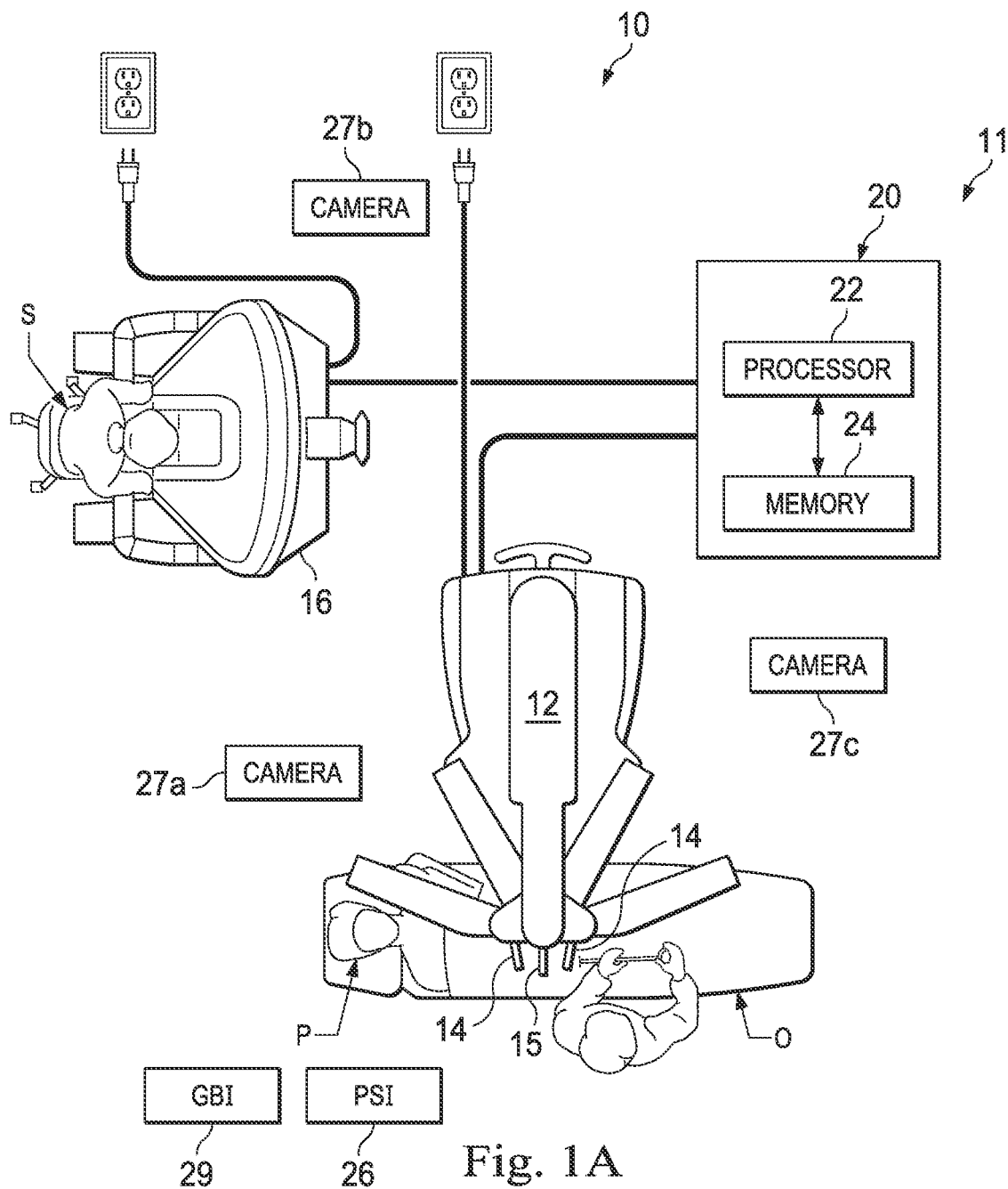
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 is positioned in a surgical environment 11 and generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperational medical system 10 also includes a control system 20. The control system 20 includes at least one memory 24 and at least one processor 22, and typically a plurality of processors, for effecting control between the medical instrument system 14, the operator input system 16, and other auxiliary systems which may include, for example, imaging systems, audio systems, fluid delivery systems, display systems, illumination systems, steering control systems, irrigation systems, and/or suction systems. The control system 20 can be used to process the images of the surgical environment from the imaging system 15 for subsequent display to the surgeon S through the surgeon's console 16. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscope imaging system 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

A surgical environment monitoring system, including one or more monitoring devices such as cameras 27a, 27b, 27c, is positioned in the surgical environment 11. The cameras 27a-c may be used to capture images in the surgical environment 11 outside of the patient P anatomy. For example and as will be described further, the cameras 27a-c may be used to monitor the extremities of the surgeon S during a procedure. The images of the surgeon's hands and feet may be presented to the surgeon through a display at the console 16 to assist the surgeon during transitions that require movement of the extremities to control operation of the system 10. The cameras 27a-c may also or alternatively be used to capture images of the external patient anatomy, the teleoperational assembly, other equipment in the surgical environment, and personnel in the surgical environment. The cameras 27a-c may be mounted in any of a variety of ways including on discrete pedestals or tripods, from the ceiling, on equipment in the surgical environment including the orienting platform 53, on the shafts of the instruments 14 or endoscope 15 external of the patient anatomy, or on equipment worn by the surgeon S or by other personnel in the surgical environment, such as a head-mounted camera.

A gesture-based interface (GBI) 29 may also be located in the surgical environment 11. The GBI may be a touch-based interface system such as a computer tablet or may be a three-dimensional tracking and interface system such as a Leap Motion system available from Leap Motion, Inc. of San Francisco, California or such as Kinect from Microsoft Corporation of Redmond, Washington. Additionally or alternatively, the GBI may be a wearable device such as a head-mounted device. The GBI 29 may be used to track two or three-dimensional user inputs from the surgeon S or other surgical personnel.

A patient side interface (PSI) 26 may be located or locatable near the bedside of the patient. The PSI 26 may allow the surgeon S to approach the patient and still have access to at least some functionality of the console 16 or additional inputs not available at the console 16. The PSI 26 may include a display for displaying similar or different images from those displayed at the console 16. The PSI 26 may include a head-mounted display system, a boom-mounted display system, or a dome-style display system that provides primary and peripheral images or 360° images of the surgical environment. The PSI 26 may also include a user input device such as a computer tablet, trackball, or three-dimensional input system. In some embodiments, the PSI 26 may include all or some components of the GBI 29.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be co-located, or they may be positioned in separate locations. Multiple operator input systems allow more than one operator to control one or more manipulator assemblies in various combinations.

Figure 1B:
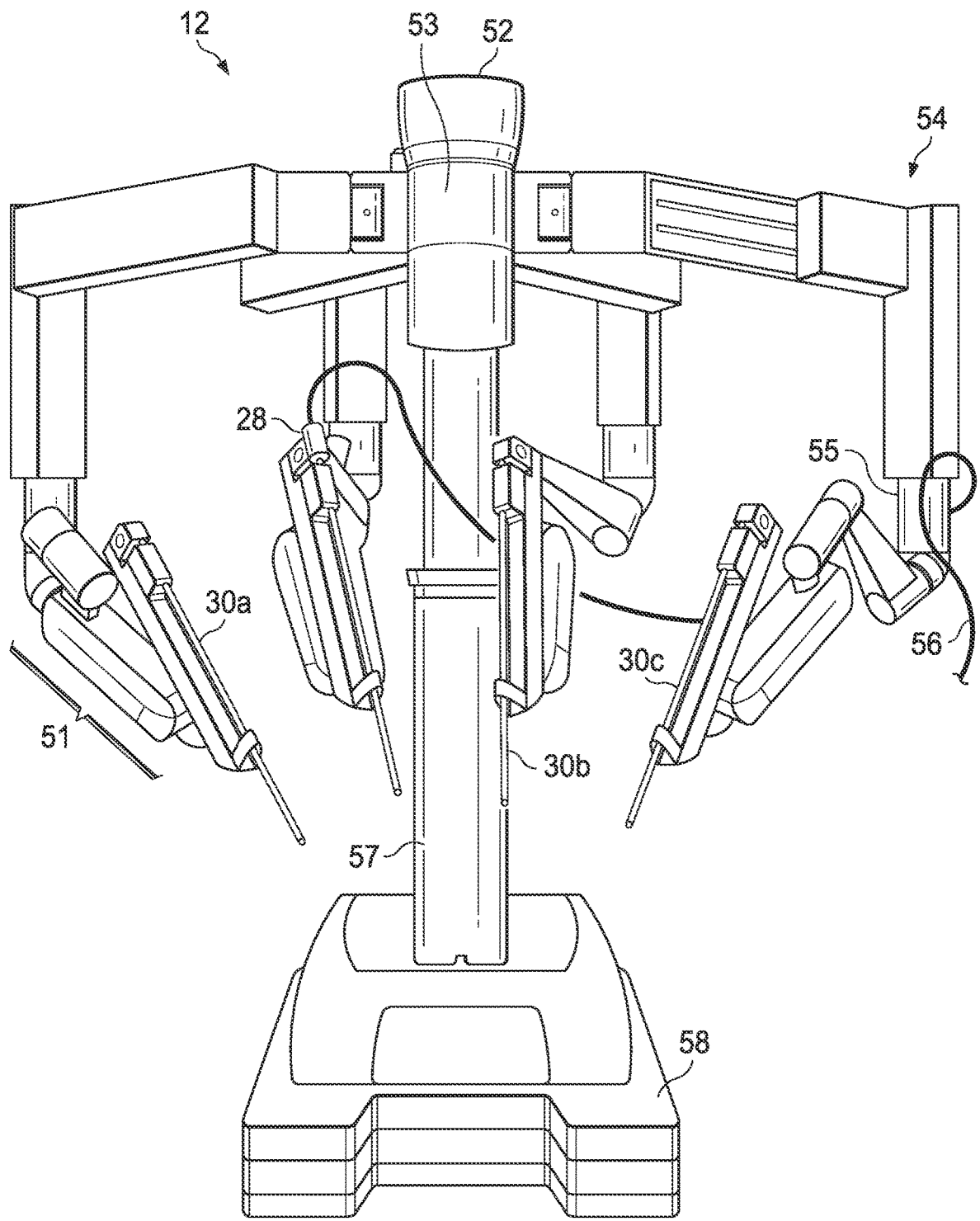
FIG. 1B is a perspective view of a teleoperational manipulator, according to one example of principles described herein.

FIG. 1B is a perspective view of one embodiment of a teleoperational assembly 12 which may be referred to as a patient side cart. The patient side cart 12 shown provides for the manipulation of three surgical tools 30a, 30b, 30c (e.g., instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical environment within the patient anatomy can include images of the distal ends of the surgical tools 30a-c when they are positioned within the field-of-view of the imaging device 28.

The patient side cart 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 12 may also include a telescoping horizontal cantilever 52 for moving the orienting platform 53 in a horizontal direction.

In the present example, each of the arms 54 connects to a manipulator arm 51. Each manipulator arms 51 may connect to a respective one of the medical tools 30a-c or to the imaging device 28. The manipulator arms 51 may be teleoperable. In some examples, the arms 54 connecting to the orienting platform are not teleoperable. Rather, such arms 54 are positioned as desired before the surgeon 18 begins operation with the teleoperative components.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
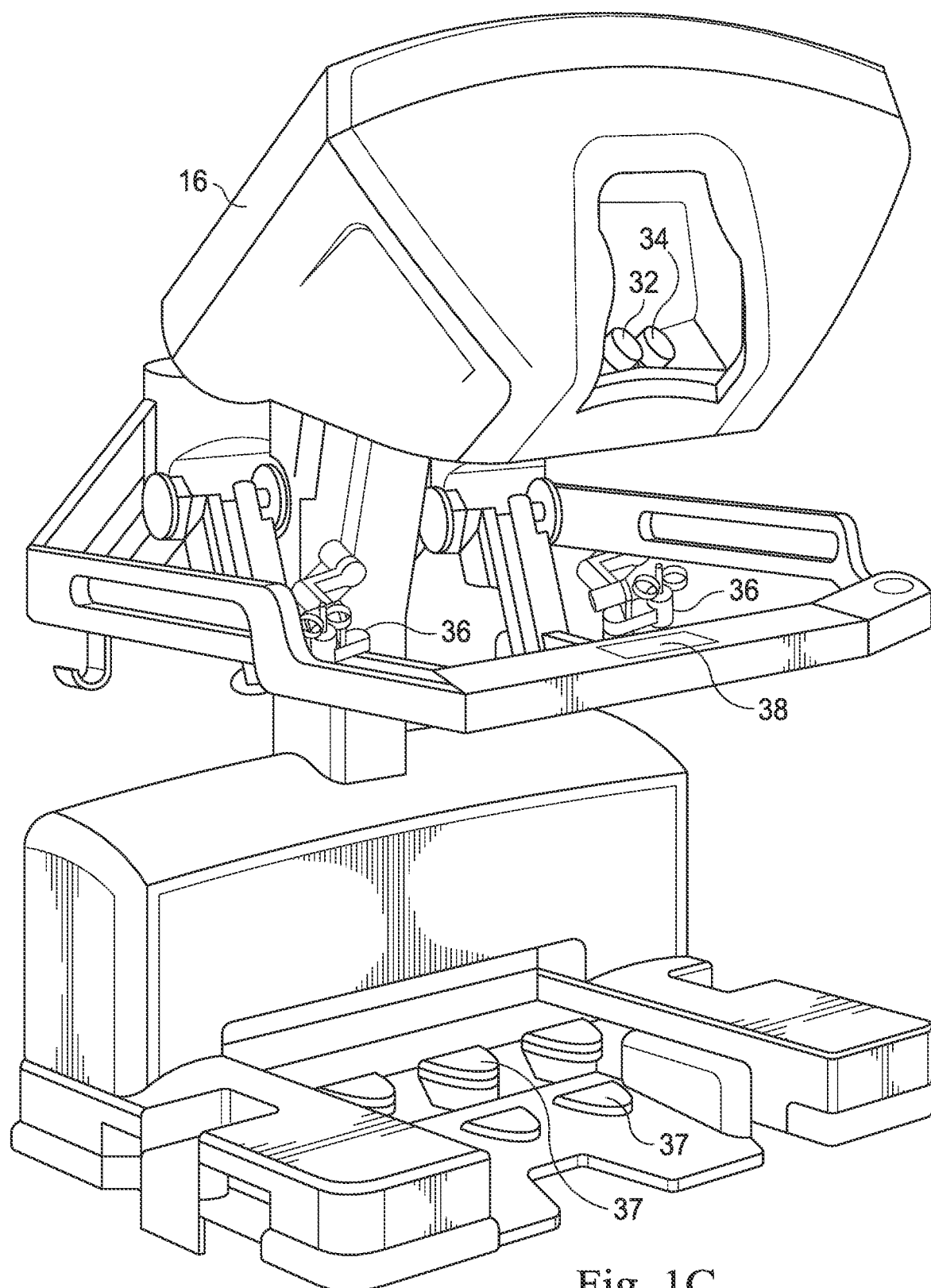
FIG. 1C is a perspective view of a surgeon's control console for a teleoperational medical system, in accordance with many embodiments.

FIG. 1C is a perspective view of the surgeon's console 16. The surgeon's console 16 includes a left eye display 32 and a right eye display 34 for presenting the surgeon S with a coordinated stereo view of the surgical environment that enables depth perception. The displayed image of the surgical environment may be obtained from an imaging system such as the endoscopic imaging system. Additionally or alternatively, the displayed image of the surgical environment may include images from anatomic models created from pre-operative or intra-operative image data sets. Pre-operative or intraoperative image data set of the patient anatomy may be obtained using external or non-invasive imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite models representing a partial or an entire anatomical organ or anatomical region. An image data set is associated with the composite representation. The images used to generate the composite representation may be recorded preoperatively or intra-operatively during a clinical procedure. The pre-operative or intra-operative image data may be presented as two-dimensional, three-dimensional, or four-dimensional (including e.g., time based or velocity based information) images or as images from models created from the pre-operative or intra-operative image data sets. Images from different imaging modalities may be displayed one at a time (e.g., the surgeon may toggle through the different modality images), may be displayed in parallel (e.g., in multiple windows of a composite display) or one may be overlaid or superimposed on the other.

The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot. Optionally, input control device 38 may include a touch-based input device such as a computer tablet. Optionally, a gesture-based interface may be included in the console 16.

During a teleoperational procedure, entirely virtual and/or augmented reality images may be provided to the surgeon S and/or other surgical personnel to provide a more extensive view of the surgical environment, provide additional information about the patient or the procedure, and/or provide additional controls for use during the procedure. Various systems and methods for providing virtual or augmented reality images during a teleoperational procedure are disclosed in U.S. Pat. No. 8,520,027, filed May 14, 2010, disclosing "Method and System of See-Through Console Overlay;" International Publication Number WO 2014/176403, filed Apr. 24, 2014, disclosing "Surgical Equipment Control Input Visualization Field;" U.S. Pat. No. 8,398,541, filed Aug. 11, 2008, disclosing "Interactive User Interfaces for Robotic Minimally Invasive Surgical Systems;" U.S. Pat. No. 9,788,909, filed Nov. 11, 2013, disclosing "Synthetic Representation of a Surgical Instrument;" and U.S. Pat. No. 9,858,475, filed May 14, 2010 disclosing "Method and System of Hand Segmentation and Overlay Using Depth Data," which are incorporated by reference herein in their entirety.

Figure 2:
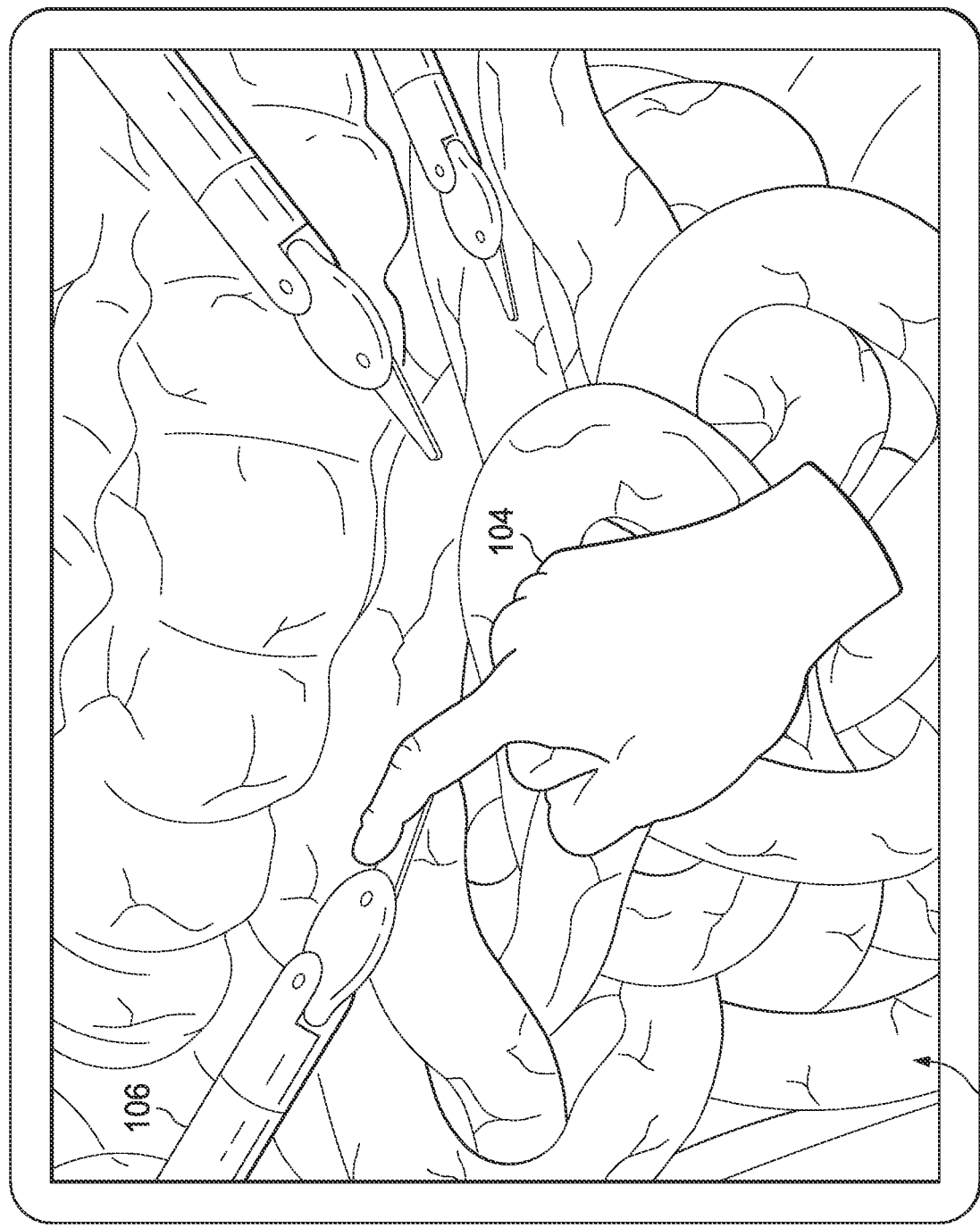
FIG. 2 illustrates a surgical environment image augmented with an image of a user's extremity.

FIG. 2 is a display 100 illustrating surgical environment image 102, which in this example is an interior patient anatomy image obtained by an endoscopic imaging system (e.g., system 15, 28) augmented with a cursor image 104 of a real-time image of a user's extremity, which in this example is a right hand of the surgeon. The image of the surgeon's hand may be obtained by a camera 27a-c or by the GBI system 29 and used as a cursor to indicate the current position for interaction with an object in the image 102. The endoscopic image 102 includes an image of an instrument 106 in the surgical environment. In this example the instrument 106 is a retractor. When the teleoperational system is in an adjustment mode, the surgeon S may move his right hand, thereby moving the cursor 104 to interact with the image of the instrument 106 (e.g., a retractor), to cause an adjustment in the actual position of the retractor in the surgical environment. The cursor image 104 of the surgeon's hand allows the surgeon to visualize his hand virtually selecting and moving the retractor 106. The movement of the retractor in the surgical environment may be generated by the teleoperational system in response to the commanded motion of the surgeon's hand. In various alternative embodiments, a cursor image may be a static (i.e., previously captured) image of the user's extremity (e.g., a hand, finger, foot) or another type of static cursor symbol depicting a portion of a human anatomy (e.g., an image of an eye or a head).

Figure 3:
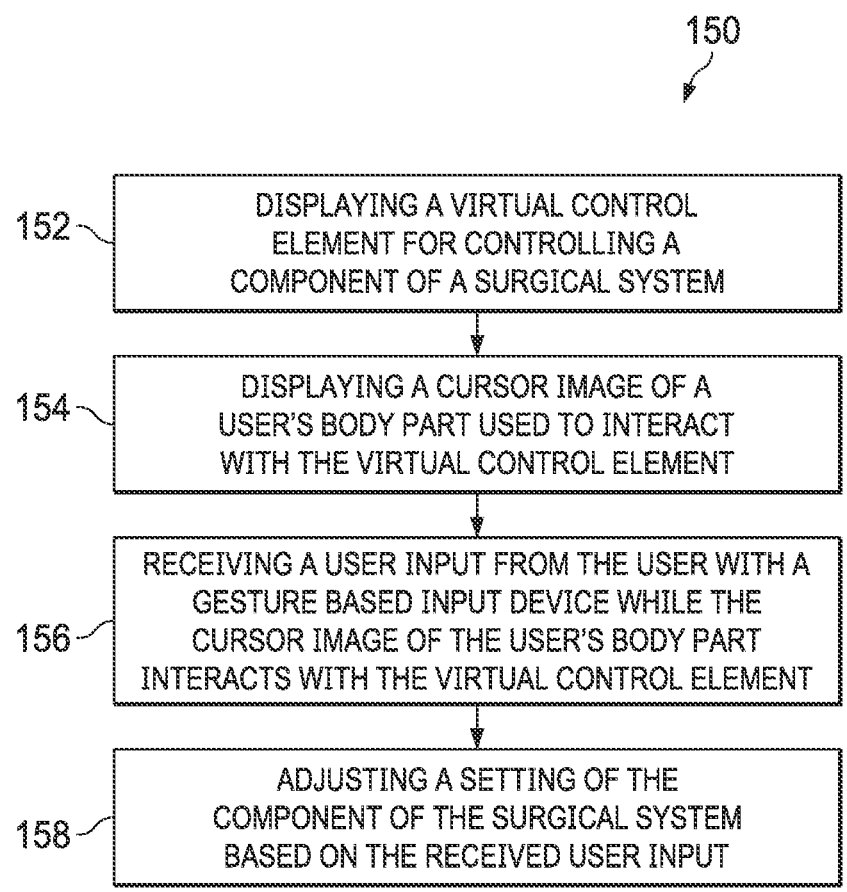
FIG. 3 illustrates a method of adjusting a virtual control element with a cursor image of a user's extremity.

FIG. 3 illustrates a method 150 of adjusting a virtual control element with a cursor image of a user's extremity. The method 150 is illustrated in FIG. 3 as a set of operations or processes. Not all of the illustrated processes may be performed in all embodiments of method 150. Additionally, one or more processes that are not expressly illustrated in FIG. 3 may be included before, after, in between, or as part of the illustrated processes. In some embodiments, one or more of the processes of method 150 may be implemented, at least in part, in the form of executable code stored on non-transitory, tangible, machine-readable media that when run by one or more processors (e.g., the processors of control system 20) may cause the one or more processors to perform one or more of the processes.

At a process 152, a virtual control element is displayed. The virtual control element may be a sliding adjuster, a toggle switch, a dial, or other element for controlling a binary system function (e.g. on/off) or a variable system function (e.g., power level, brightness level, sound level, frequency level) of a component of the teleoperational system or an auxiliary equipment component in the surgical environment. At a process 154, a cursor image of a user (e.g. the surgeon S) body part (e.g., the hand of surgeon S) used for controlling the virtual control element is displayed. At a process 156, a gesture based interface (e.g. GBI 29) receives input from the surgeon S by registering movement of the user's hand virtually manipulating the virtual control element as the real-time cursor image of the user's hand interacts with the virtual control element. At a process 158, the binary system function or variable system function is changed or adjusted based on the movement of the user's hand. The method 150 is further illustrated with reference to FIGS. 4 and 5.

Figure 4A:
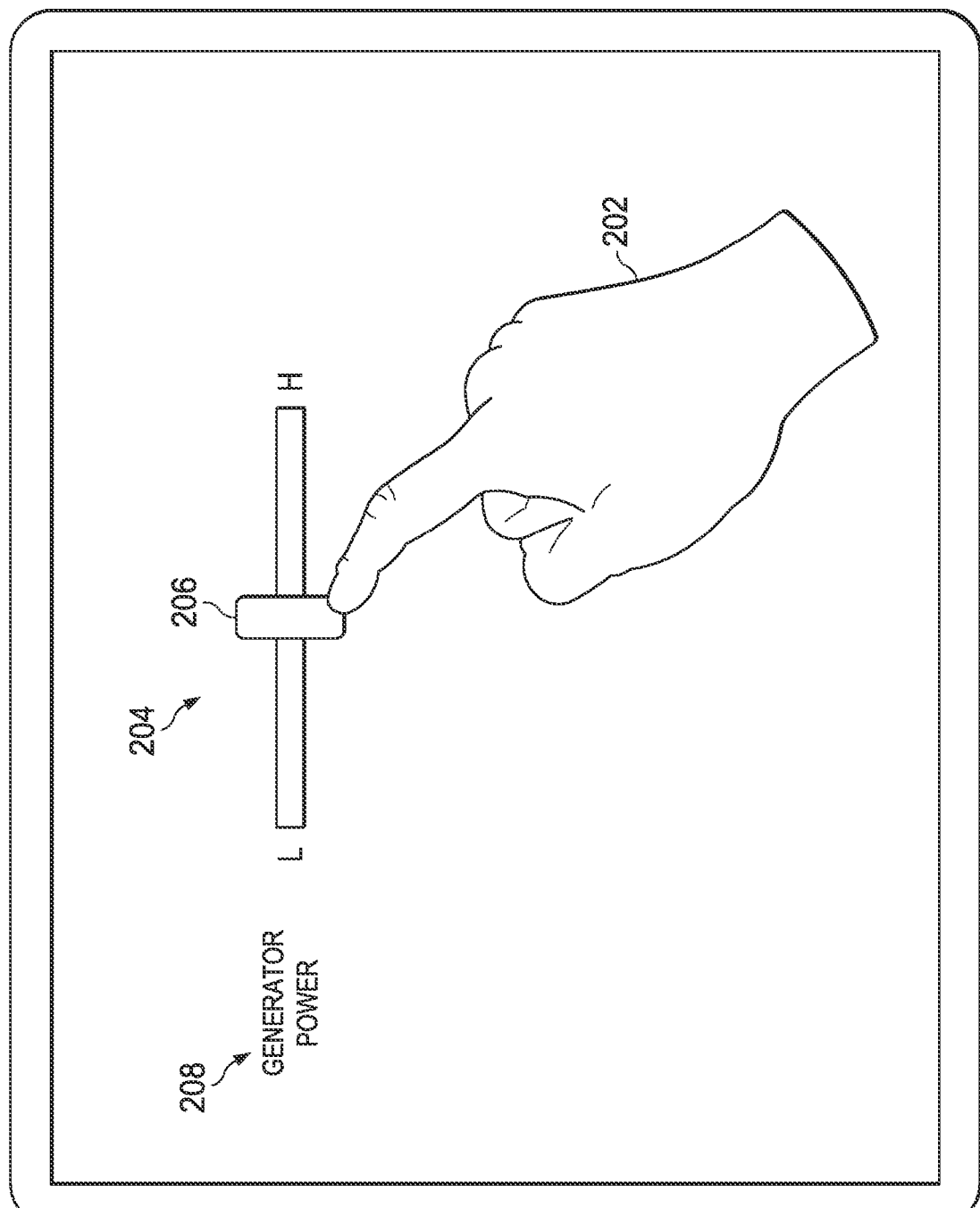
FIG. 4A illustrates a cursor image of a user's extremity interacting with a virtual control element.

With reference to FIG. 4A, an image 200 includes a cursor image of a user's extremity (e.g., a right hand) 202 interacts with a virtual control element 204, which in this example includes a virtual slider 206. A graphical element such as a graphical identifier 208 of the system controlled by the control element 204 may also be included. In this example, the identifier 208 is a textual description, but in other examples the identifier 208 may be a pictorial representation of the system controlled by the control element. In this example, the virtual control element 204 may control the variable level of power, sound, frequency, or other characteristic of an auxiliary system. The auxiliary system may be, for example, a power generator, a speaker, a display screen, or an irrigation system. As the user's hand moves the slider 206 to the right, the power level of the generator increases and as the slider moves to the left, the power level decreases. The user's hand may be tracked by a GBI or a touch-based input system. Additionally, the real-time cursor image of the user's hand 202 may be generated by a camera 27a-c to provide the user with spatial awareness of his hand relative to the virtual control element 204. Optionally, the images 202-208 may be superimposed on, integrated with, or otherwise augment an image of either the internal patient anatomy or an image of the surgical environment external of the patient anatomy.

FIG. 4B illustrates an image 220 of the real-time cursor image 202 interacting with a real-time image of an auxiliary component 222 in the surgical environment. In this example, the image 220 captures the surgical environment which includes the auxiliary component 222. The image of the auxiliary component in the image 220 serves as a virtual control element for the actual auxiliary component 222 in the surgical environment. For example, if the auxiliary component 222 is a high frequency power generator, the surgeon may gesture with his hand in a predetermined motion toward the auxiliary component 222 in the surgical environment to change the power level of the generator. An upward hand or finger gesture may correspond to an increase in power level and a downward hand or finger gesture may correspond to a decrease in power level. Alternatively, the auxiliary component 222 may include a power control knob 224, and a clockwise hand gesture toward the knob 224 may correspond to an increase in power level with a counter-clockwise hand gesture may correspond to a decrease in power level. In alternative embodiments, the auxiliary system may be, for example, a speaker, a display screen, or an irrigation system. The user's hand may be tracked by a GBI or a touch-based input system. Additionally, the real-time cursor image of the user's hand 202 may be generated by a camera 27a-c to provide the user with spatial awareness of his hand relative to the virtual control element.

Figure 5:
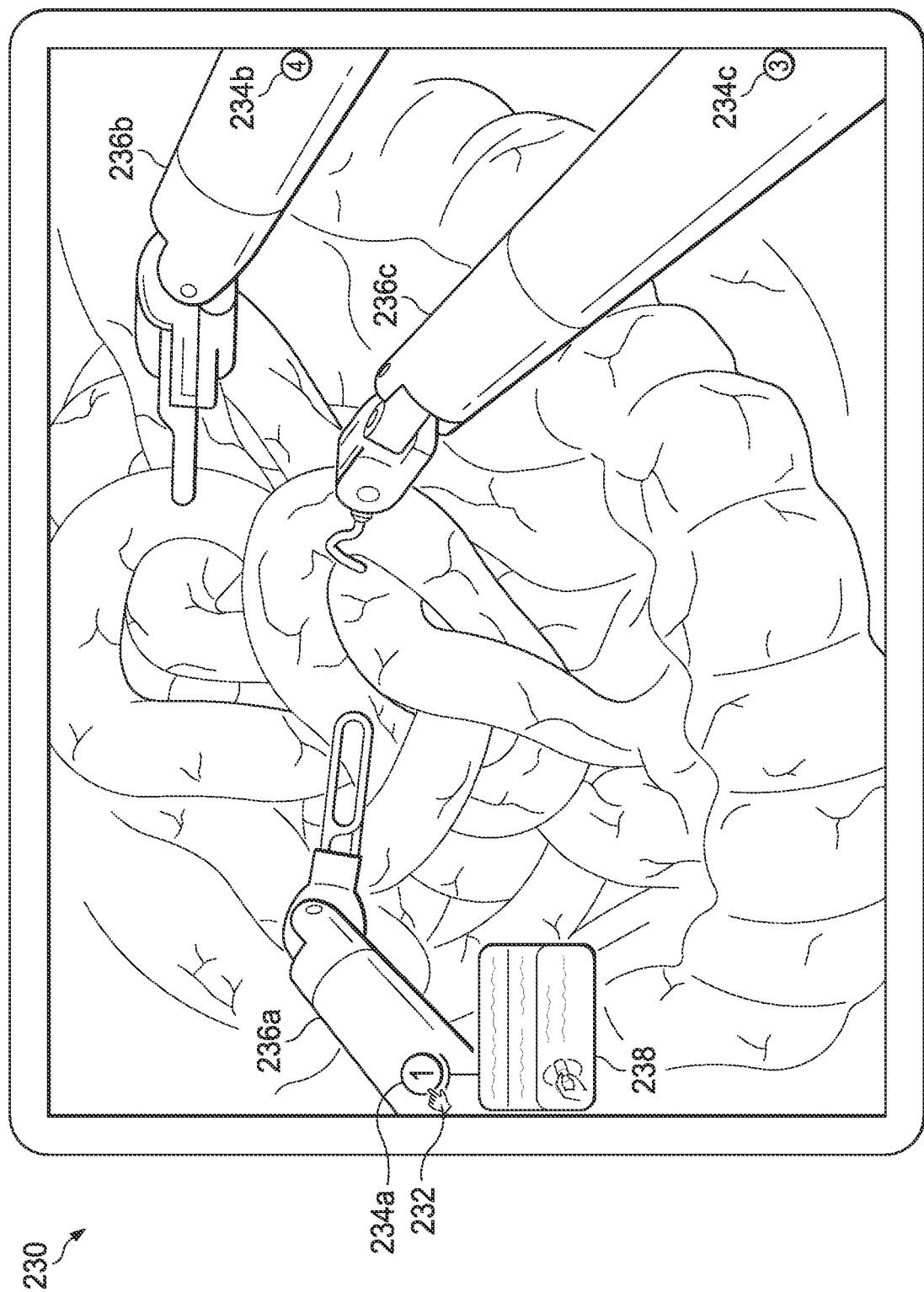
FIG. 5 illustrates a cursor image of a user's extremity interacting with an information icon.

FIG. 5 illustrates an image 230 of a surgical environment with a real-time cursor image 232 interacting with an information icon 234a displayed over the surgical environment. In this example, the image 230 captures the surgical environment which includes instruments 236a, 236b, and 236c. Information icon 234a is displayed near icon 234a. Information icon 234b is displayed near icon 234b. Information icon 234c is displayed near icon 234c. As the cursor image 232 contacts or comes into proximity with one of the information icons 234a-b, information about the respective instrument 236a-c is displayed in an information cloud. For example, information cloud 238 is displayed when the cursor image 232 interacts with the information icon 234a to provide information about the tool 236a. The provided information may include, for example, the type of instrument, the activation status of the instrument, instructions about operating or trouble-shooting the instrument, and/or buttons activatable by the cursor 232 to effect the operation of the instrument 236a.

In an alternative embodiments, the cursor image of the user's extremity may be a real-time image of the user's foot as it moves between pedal inputs 37. The real-time image of the foot and pedals may be obtained by a camera 27a-c and may be presented as a separately displayed image, as a picture-in-picture within the current endoscopic image, or behind a semi-transparent current endoscopic image to provide the surgeon with the sense that he is looking through the console 16 to view his foot as it moves toward a different pedal. In still another alternative embodiment, the image of the user's extremity may be a real-time image of the user's hand as it transitions out of or into engagement with the input control devices 36. The real-time image of the hand and control devices 36 may be obtained by a camera 27a-c and may be presented as a separately displayed image, as a picture-in-picture within the current endoscopic image, or behind a semi-transparent current endoscopic image to provide the surgeon with the sense that he is looking through the console 16 to view his hand as it moves into or out of the control device 36. Allowing the surgeon to see his hands or feet as they transition between positions may boost the surgeon's confidence that his hands and feet, which are not directly visible due to the console 16 blocking the user's view, are making the correct engagement with the input devices 36, 37.

Figure 6:
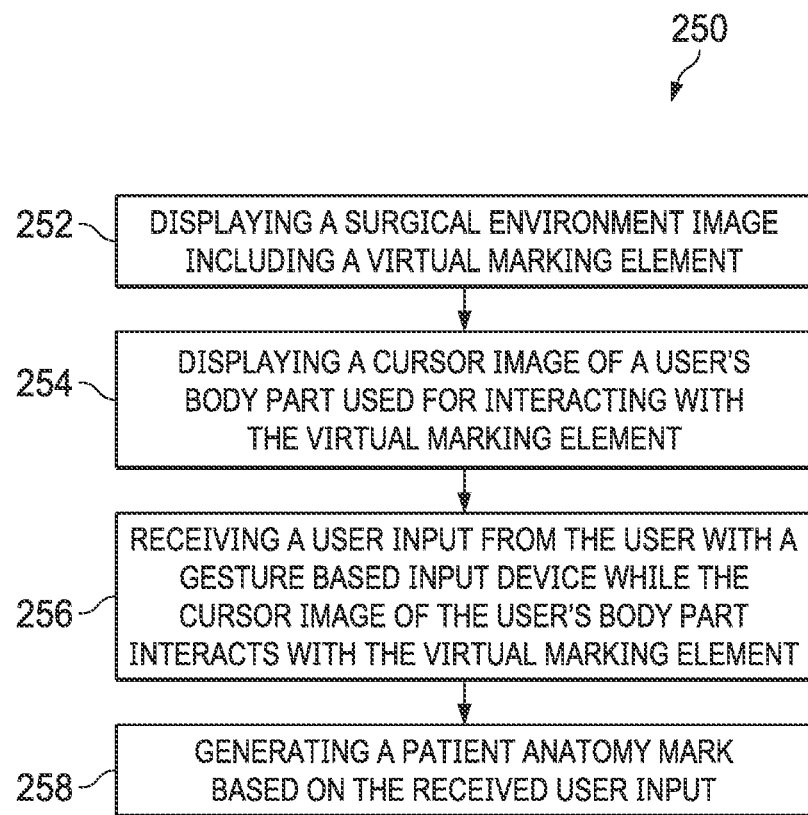
FIG. 6 illustrates a method of patient marking using a gesture based input device.

FIG. 6 illustrates a method 250 of patient marking using a gesture based input device. The method 250 is illustrated in FIG. 6 as a set of operations or processes. Not all of the illustrated processes may be performed in all embodiments of method 250. Additionally, one or more processes that are not expressly illustrated in FIG. 6 may be included before, after, in between, or as part of the illustrated processes. In some embodiments, one or more of the processes of method 250 may be implemented, at least in part, in the form of executable code stored on non-transitory, tangible, machine-readable media that when run by one or more processors (e.g., the processors of control system 20) may cause the one or more processors to perform one or more of the processes.

At a process 252, a surgical environment including a virtual marking element is displayed. The virtual marking element may be used, for example, to indicate the surgeon's preferred entry port locations or may mark anatomic features of the patient. At a process 254, a cursor image of a user (e.g. the surgeon S) body part (e.g., the hand of surgeon S) used for interacting with the virtual marking element is displayed. At a process 256, a gesture-based interface (e.g. GBI 29) receives input from the surgeon S by registering movement of the user's hand virtually interacting with the marking element as the real-time cursor image of the user's hand interacts with the virtual marking element. For example, the movement of the user's hand may be used to create a new marker or move a marker from a default location. At a process 258, the patient anatomy is marked (e.g. with light, ink, or other marking material) based on the position of the marking element. The method 250 is further illustrated with reference to FIG. 7.

Figure 7:
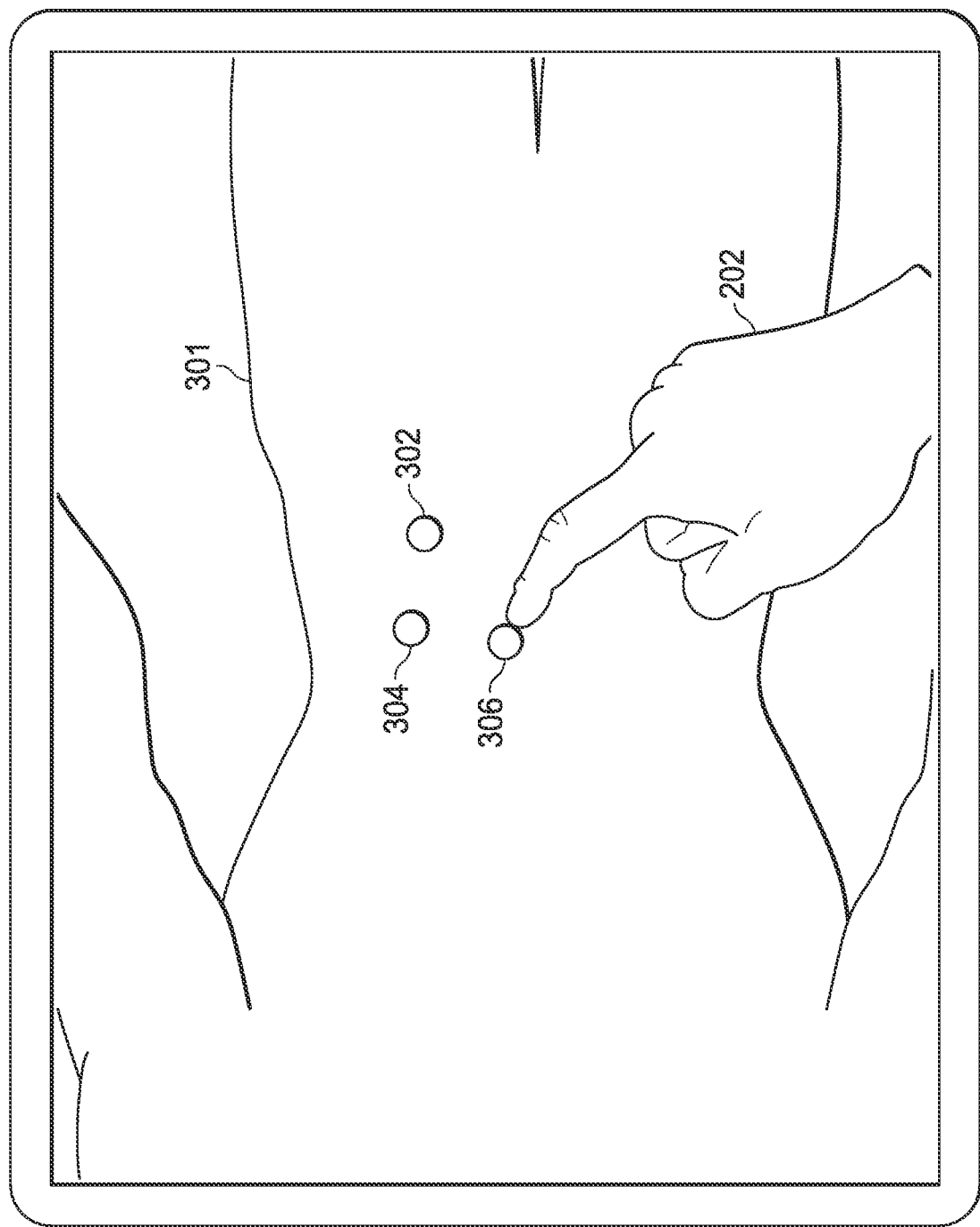
FIG. 7 illustrates an image of a surgical environment with a cursor image of a user's extremity interacting with an image of marking elements.

With reference to FIG. 7, a surgical environment image 300 includes an exterior image 301 of a patient anatomy. A cursor image of a user's extremity (e.g., a right hand) 202 interacts with virtual marking elements 302, 304, 306. The virtual marking elements may be created by a gesture of the user's hand or may be created in a default location. The user's hand may interact with a virtual marking element 306 to move the marking element to a different location than where it was originally created. In this example the virtual marking elements 302, 304, 306 may be used to mark port locations on the image 301 of the patient anatomy. The virtual marking elements be virtually dragged relative to the image 301 of the patient anatomy by the tracked motion of the user's hand. The user's hand may be tracked by a GBI or a touch-based input system. Additionally, the real-time cursor image of the user's hand 202 may be generated by a camera 27a-c to provide the user with spatial awareness of his hand relative to the virtual marking elements 302, 304, 306. After the virtual marking elements 302, 304, 306 are established relative to the image 301 of the patient anatomy, corresponding actual marks may be made with light, ink, or another marking medium on the anatomy of the patient to mark the locations of entry ports prior to a surgical procedure. The visual marking elements may, for example, indicate candidate incision locations which may be evaluated by the control system to provide feedback on the feasibility of the incision locations by evaluating reachable workspace and the likelihood of internal or external collisions. The virtual marking elements and the surrounding areas may be color coded based on the predicted feasibility measures.

Figure 8:
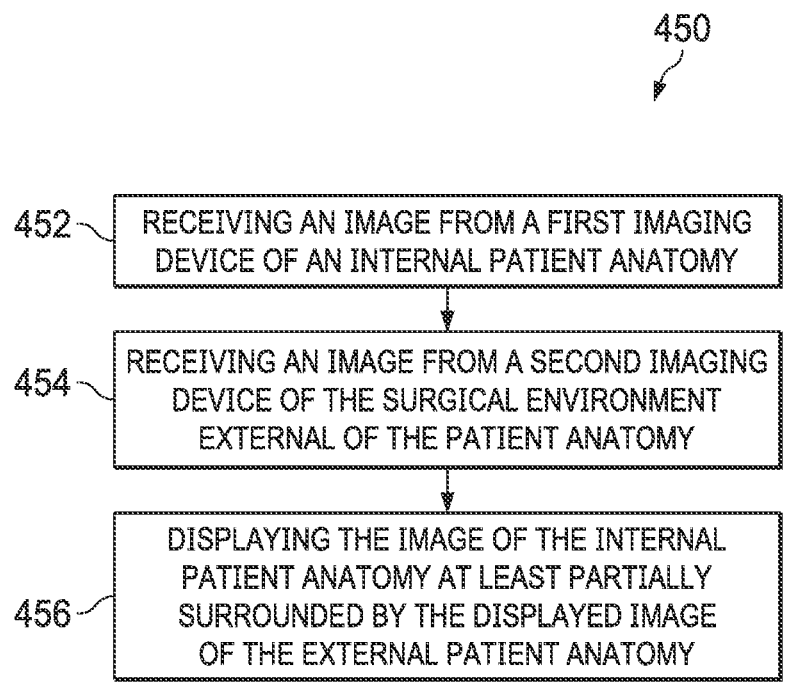
FIG. 8 illustrates a method of displaying an image of the internal patient anatomy at least partially surrounded by the displayed image of the external patient anatomy.

FIG. 8 illustrates a method 450 of displaying an image of an internal patient anatomy at least partially surrounded by the displayed image of the external patient anatomy. The method 450 is illustrated in FIG. 8 as a set of operations or processes. Not all of the illustrated processes may be performed in all embodiments of method 450. Additionally, one or more processes that are not expressly illustrated in FIG. 8 may be included before, after, in between, or as part of the illustrated processes. In some embodiments, one or more of the processes of method 450 may be implemented, at least in part, in the form of executable code stored on non-transitory, tangible, machine-readable media that when run by one or more processors (e.g., the processors of control system 20) may cause the one or more processors to perform one or more of the processes.

Figure 9:
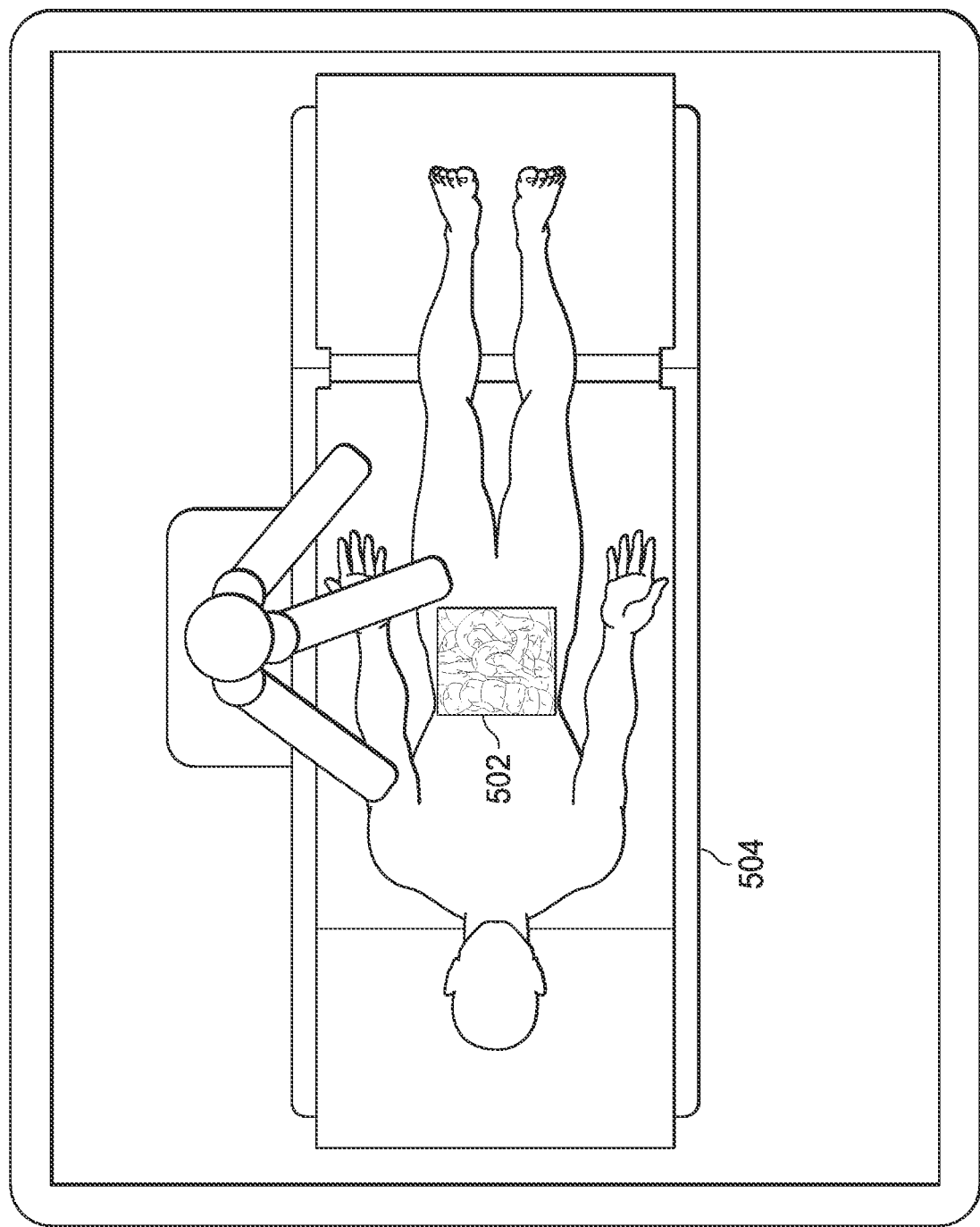
FIG. 9 illustrates an image of the internal patient anatomy at least partially surrounded by the displayed image of the external patient anatomy.

At a process 452, a first image from a first imaging device is received. The first image may be an internal view of the patient anatomy, received, for example, from an endoscopic device. At a process 454, a second image from a second imaging device is received. The second image may be an external view of the patient anatomy and/or the surgical environment surrounding the patient anatomy. At a process 456, the first image is displayed in spatial context relative to the second image. For example, as shown in FIG. 9, a display 500 includes an image 502 of the internal patient anatomy at least partially surrounded by the displayed image 504 of the external patient anatomy. The image 502 may be obtained by an endoscopic imaging system (e.g., system 15, 28), and the image 504 may be obtained by an imaging system such a camera 27a-c. The viewing orientation of the internal and external views may be aligned. For example, the external view may be digitally rotated to share the same roll angle as the internal (e.g., endoscopic) view. Additionally or alternatively, the pitch and/or yaw of the external view may be aligned with the viewing direction of the internal view so that internal and external motions can be intuitively controlled from the same reference frame.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
 a processor; and
 a memory having computer readable instructions stored thereon, the computer readable instructions, when executed by the processor, cause the system to:
  display an image of a surgical environment, wherein the image includes an information icon corresponding to an instrument in the surgical environment;
  display an image of a body part of a user, the image of the body part used to interact with the information icon;
  receive a gesture of the body part of the user, via a gesture based input device registering movement of the body part of the user, to cause the image of the body part to interact with the information icon; and
  display an information menu in the image of the surgical environment based on the interaction between the image of the body part and the information icon.

2. The system of claim 1, wherein the image of the body part interacts with the information icon when the image of the body part contacts the information icon.

3. The system of claim 1, wherein the image of the body part interacts with the information icon when the image of the body part is within close proximity to the information icon.

4. The system of claim 1, wherein the information menu includes information about the instrument.

5. The system of claim 4, wherein the information about the instrument comprises at least one of an instrument type, an activation status of the instrument, or operating instructions for the instrument.

6. The system of claim 1, wherein the information menu includes one or more graphical elements activatable by the image of the body part of the user.

7. The system of claim 6, wherein when the graphical elements are activated by the image of the body part, an operation of the instrument is effected.

8. The system of claim 1, further comprising the gesture based input device, wherein the gesture based input device is configured to receive a three dimensional user input.

9. The system of claim 1, further comprising the gesture based input device, wherein the gesture based input device includes at least one of a tablet device or a user wearable device.

10. The system of claim 1, wherein the body part used to provide input to the gesture based input device is at least one of a user hand or a user foot.

11. The system of claim 1, wherein the image of the surgical environment is displayed on at least one of a head-mounted display device or a patient-side device.

12. The system of claim 1, wherein the image of the surgical environment is an endoscopic image inside a patient anatomy.

13. The system of claim 1, wherein the image of the surgical environment is an external image of a patient anatomy.

14. The system of claim 1, wherein the information icon is overlaid over an image of the instrument in the surgical environment.

15. The system of claim 1, wherein the information menu is displayed near the information icon.

16. The system of claim 1, wherein the image of the surgical environment further includes a second information icon corresponding to a second instrument in the surgical environment, and wherein the image of the body part is further used to interact with the second information icon.

17. The system of claim 16, wherein the instructions further cause the system to:
 receive a second gesture of the body part of the user, via the gesture based input device, to cause the image of the body part to interact with the second information icon; and
 display a second information menu in the image of the surgical environment based on the interaction between the image of the body part and the second information icon.

18. The system of claim 17, wherein the second information menu includes information about the second instrument, and wherein the information about the second instrument comprises at least one of an instrument type, an activation status of the second instrument, or operating instructions for the second instrument.

19. The system of claim 17, wherein the second information menu includes one or more graphical elements activatable by the image of the body part of the user, and wherein when the graphical elements are activated by the image of the body part, an operation of the second instrument is effected.

20. The system of claim 16, wherein the information icon is overlaid over an image of the instrument in the surgical environment, and wherein the second information icon is overlaid over an image of the second instrument in the surgical environment.

* * * * *